United States Patent [19]

Heyler, III

[11] Patent Number: 5,033,481
[45] Date of Patent: Jul. 23, 1991

[54] INTRAOPERATIVE OR INTEROPERATIVE LONGITUDINAL TISSUE EXPANDER

[75] Inventor: Charles J. Heyler, III, Carpinteria, Calif.

[73] Assignee: Inamed Development Company, Carpinteria, Calif.

[21] Appl. No.: 596,488

[22] Filed: Oct. 12, 1990

[51] Int. Cl.⁵ .............................................. A61F 2/12
[52] U.S. Cl. ........................................ 623/8; 128/899; 623/11; 606/191
[58] Field of Search ............... 128/DIG. 20, 898, 899; 623/8, 11, 12; 606/191, 192, 151, 152, 155

[56] References Cited

U.S. PATENT DOCUMENTS 4,863,469  9/1989  Van Beek et al.
4,899,764  2/1990  Gauger et al. ..................... 128/899
4,950,292  8/1990  Audretsch ............................ 623/8

Primary Examiner—Randall L. Green
Assistant Examiner—Trinh Nguyen
Attorney, Agent, or Firm—Michael G. Petit

[57] ABSTRACT

An improved inflatable longitudinal expander used in reconstructive surgery for lengthening soft tissue. A retaining disk, a central portion of which is affixed to the top of an inflatable expansion chamber, wraps around and securely holds the soft tissue to be expanded. The retaining disk is fastened in place with a single suture. Once the soft tissue is safely enclosed within the envelope formed by the retaining disk, the tissue expander is inflated with saline solution injected through a self-sealing injection port causing the inflatable expansion chamber to expand and the soft tissue to be stretched and lengthened. The expander, which may be used intraoperatively or implanted for interoperative use, is particularly adapted for either short or long-term stretching of tubular or linear tissues such as blood vessels, fallopian tubes or nerves.

4 Claims, 2 Drawing Sheets

INTRAOPERATIVE OR INTEROPERATIVE LONGITUDINAL TISSUE EXPANDER

FIELD OF THE INVENTION

This invention relates to a device for the expansion or elongation of soft linear tissue and more particularly to a retaining disk on an inflatable chamber for positionally accommodating a soft tissue during elongation.

DESCRIPTION OF THE PRIOR ART

Soft tissue generally have some elasticity which permits their length to be increased. While each tissue is different, most are sufficiently complex to have at least several different interior anatomical layers as a lining which may not tolerate strong compressive or gripping forces. Some tissue may tear if expanded too quickly while others may respond favorably to expansion over a very short period of time. Most tissue has sufficient elasticity and yield that an extension of as much as fifty percent can be attained. If such expansion can be achieved over a relatively short period of time, say perhaps one hour, then the device is termed an intraoperative tissue expander. If the stretching or elongation of the tissue must take place much more slowly over a much longer period of time, then the expander must be implanted. This type of expander is termed an interoperative tissue expander. Both types of tissue expanders, that is: interoperative and intraoperative, are well known in the art but such prior art devices have their shortcomings.

Of particular interest are longitudinal nerve expanders placed under a nerve for purposes of nerve expansion. Such nerve expanders have consisted primarily of skin flap expanders, designed for stretching the skin, a planar tissue, to generate grafting skin or the like. Upon expansion of such nerve expanders, the nerve placed over the nerve expander would often disengage itself from its position over the nerve expander, and slide off the expander rendering the procedure useless until the nerve was replaced on top of the nerve expander again causing an undue waste of surgery time, effort and energy during the reconstructive process.

Van Beek et al, in U.S. Pat. No. 4,863,469, incorporated herein by reference, overcomes the disadvantages of the prior art nerve expanders by providing a saddle on top of an inflatable expansion chamber which guides or holds a nerve on the inflatable expansion member. A Van Beek nerve expander is substantially an expandable elastomer chamber with a saddle on top, the saddle housing a groove which holds the tissue to the nerve to be stretched. The chamber is in fluid communication with an injection port located directly under the surface of the skin.

Van Beek et al teach the use of an interoperative nerve expander for the long term expansion of nerves. A problem encountered with the Van Beek expander is the design of the saddle containing the groove affixed to the top of the expansion chamber. As the expansion chamber is gradually filled with fluid, the upper saddle-shaped surface, which is affixed to the uppermost surface of the expansion chamber substantially over the entire chamber-contacting surface, flattens out and actually arches to become convex. When the expansion chamber is fully inflated, the groove distorts and becomes very shallow permitting the nerve to slip therefrom. The present invention overcomes the disadvantage of prior art devices by providing a soft tissue expander with a retaining disk affixed to the apex of an expansion member which guides or holds the soft tissue over the inflatable expansion member even when the expansion member is fully inflated.

SUMMARY OF THE INVENTION

The general purpose of the present invention is to provide a low profile soft tissue expander with a retaining disk to hold the tissue in position during surgical expansion, either interoperatively or intraoperatively. The target tissue, that is: the tissue to be expanded, is held securely in place with the current invention irrespective of the degree of inflation of the expansion chamber.

According to one embodiment of the present invention, there is provided a low profile tissue expander including a retaining disk on the upper surface of an inflatable expansion chamber. The retaining disk is substantially planar and has a surface area, only a small portion of which surface area is affixed to the top surface of an inflatable expansion chamber. In the most preferred embodiment, the retaining disk is affixed to the underlying expansion chamber only near the center of the retaining disk. This enables the edges of the retaining disk to be folded up to securely envelop and hold a target tissue (the tissue to be expanded) which becomes sandwiched therein. The edges of the retaining disk enveloping the target tissue are preferably brought together and securely fastened by means of a suture. The retaining disk thus enveloping the tissue prevents the tissue from slipping from the top surface of the inflatable expansion member as the expansion chamber is inflated.

A significant aspect and feature of the present invention is the retaining disk affixed to the surface of an inflatable expansion chamber to prevent tissue enclosed therein from slipping during reconstructive expansion.

Another aspect of this invention is the attachment of the retaining disk to only a small area on the top surface of the inflatable expansion chamber which attachment prevents the retaining disk from becoming distorted during expansion.

A further object of the present invention is a soft tissue expander with a substantially rigid but malleable backing which is textured to prevent slipping against underlying surfaces.

DESCRIPTION OF THE PREFERRED EMBODIMENTS

Figure 1:
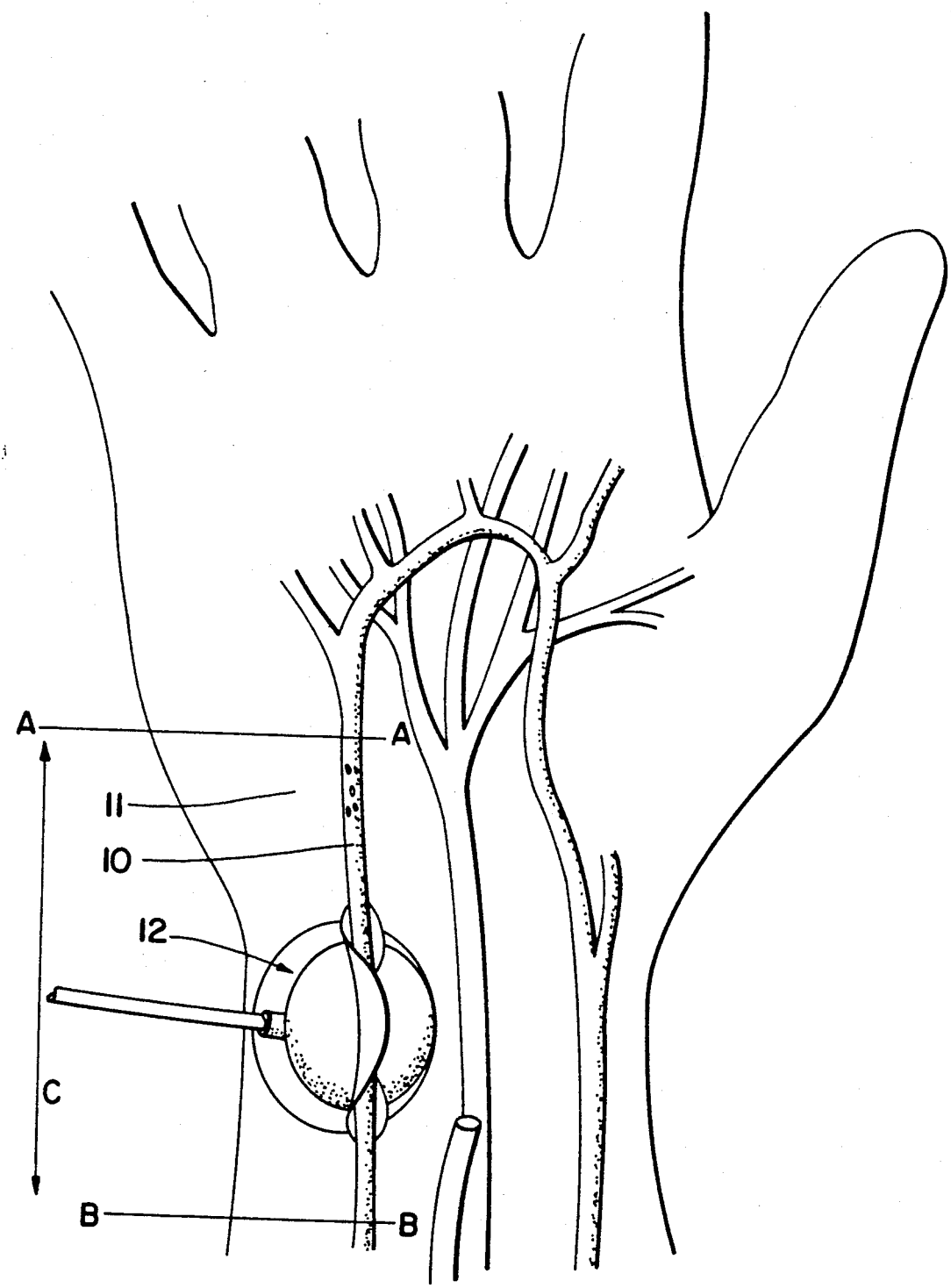
FIG. 1 illustrates a perspective view of the tissue expander of the present invention being placed beneath a blood vessel in the wrist.

In FIG. 1, it is necessary and desirable to elongate a blood vessel 10 in the wrist. The blood vessel 10 can be viewed as elongate soft tissue overlying a supporting substratum 11 which may comprise bone, muscle, tendons and the like. It is desirable to elongate the blood vessel 10 between points A and B which points may be near a defective site in the blood vessel which requires replacement by grafting. Initially, the length of the blood vessel 10 between points A and B is indicated by C. In order to elongate segment A-B a tissue expander generally indicated at 12 is placed between the segment A-B and the underlying anatomical support tissue 11.

Figure 2:
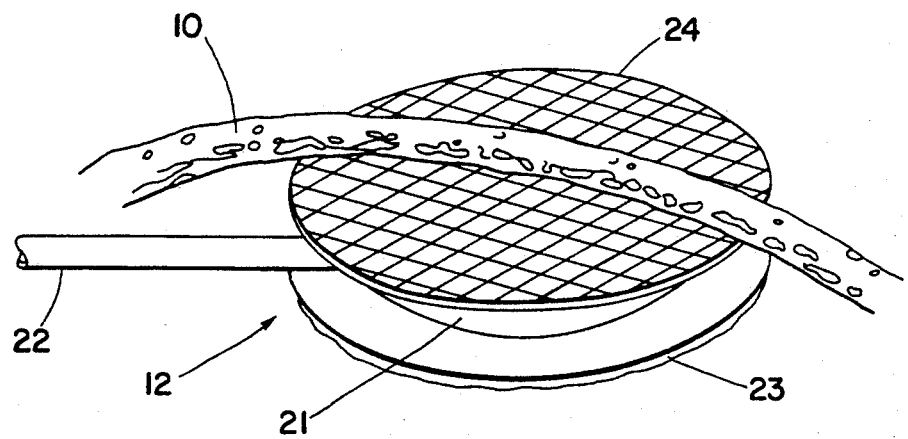
FIG. 2 is a perspective view of the tissue expander in position prior to the folding over of the retaining disk.

Turning now to FIG. 2, the longitudinal tissue expander of the present invention (12) is shown properly positioned for expansion beneath the blood vessel 10 and the underlying support tissue (not shown). The tissue expander comprises an inflatable expansion chamber 21, the interior chamber of which is in fluid communication with an external reservoir (not shown) by means of a fill tube 22 which is well known in the art. The expansion chamber 21 has a base 23 which rests against the underlying anatomical support tissue, and a flexible retaining disk 24 which is affixed to the top of the expansion chamber.

It is noted that both the blood vessel 10 and underlying tissue 11 are slippery. In the preferred embodiment of the present invention, the base 2 is textured on its underlying surface to prevent slippage of the expander during inflation. In addition to texturing, the base is reinforced with polyethylene-terephthalate fiber or some other biocompatible support material to facilitate placement of sutures (not shown) through the base to immobilize the expander 12 with respect to the underlying tissue 11.

In the cited prior art expander, a notched elastomeric saddle is bonded to the expansion chamber to positionally accommodate the member to be expanded during expansion. The problem with the notched saddle is that when the expansion chamber is inflated, the saddle, which is bonded to the entire top surface of the expansion chamber, deforms at the apex, pushing up high where the notch is cut deep (i.e. where the saddle is the thinnest) and is scarcely deformed at all where the saddle is the thickest. Thus, during inflation, the notch flattens out and the member may slip therefrom.

Figure 3:
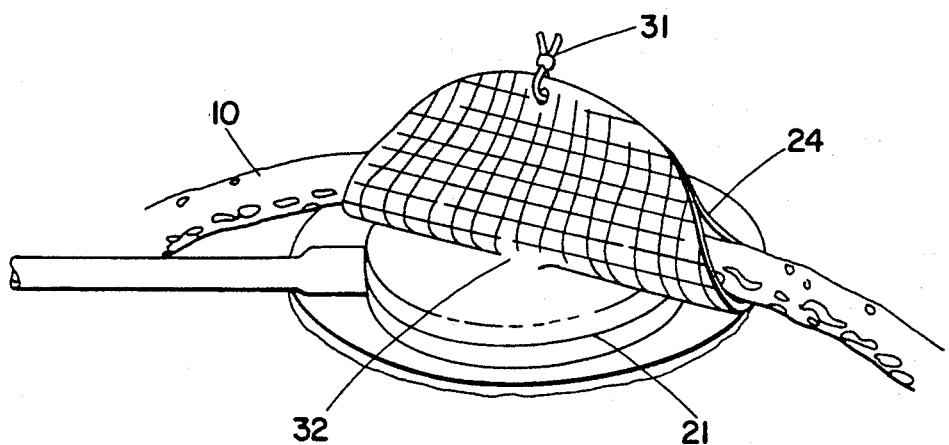
FIG. 3 shows the retaining disk folded over the soft tissue to be expanded and secured with a suture.

To overcome this problem, the present invention employs a flexible, Dacron reinforced retaining disk bonded to the apex of the expansion chamber. FIG. 3 shows the retaining disk 24 folded around the blood vessel to enclose it and fastened in its enveloping position around the blood vessel by means of a suture 31. It is an important aspect of this invention that the retaining disk 24 is affixed to the exterior apical surface of the underlying expansion chamber 21 over a small area indicated at 32. In this way, substantial deformation of the retaining disk 24 is prevented during inflation. It is important to prevent deformation of the retaining disk during expansion for the following reason.

Most soft tissue is composed of at least several layers of cells of diverse function. Each cell type has a varying susceptibility to irreversible damage by stretching or compression. Thus, it is important that the considerable tangential forces applied to the exterior surface of the member being expanded be distributed over as large a surface area as possible to minimize the pressure on any particular segment of the expanded member. If the retaining disk is bonded to the upper surface of the expansion chamber over a large area, the disk may undergo deformation during expansion thereby presenting an irregular, kinked and disk continuously smooth surface to the overlying envelope member being elongated. Such irregularities can result in unequal distribution of pressure to the enclosed area being expanded with concomitant cell damage.

Figure 4:
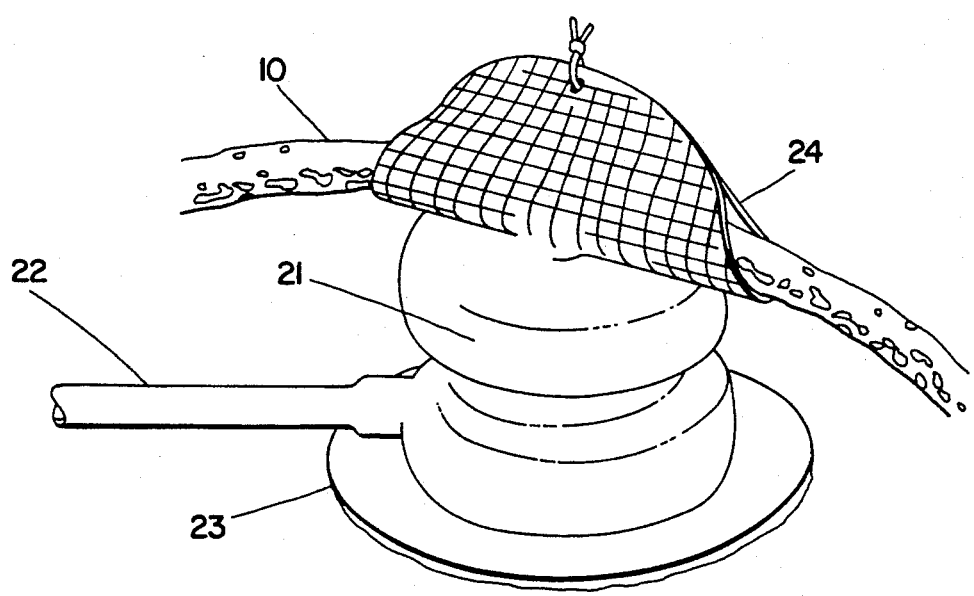
FIG. 4 shows the expansion chamber fully expanded and the soft tissue still securely held within the retaining disk.

FIG. 4 shows how the shape of the retaining disk is retained even when the expansion chamber 21 is fully inflated. With the base 23 sutured in position to the underlying support tissue and the retaining disk 24 securely enveloping the member to be elongated 10, there is no possibility of slippage of the elements with respect to one another. This is particularly important when the expander is to be used interoperatively to elongate tissue. Since the expander is implanted, perhaps for months, it is crucial that there is no slippage of elements during the slow inflation/elongation process.

It should be understood that the choice of a blood vessel for expansion, as illustrated herein, is arbitrary and given by means of example only. This invention is intended to be useful for expanding other longitudinal soft tissue as well, such as fallopian tubes and nerves. This invention is not to be limited to the specific embodiment presented but only in accordance with the scope of the appended claims.

What I claim is:

1. An improved longitudinal tissue expander for elongation of more or less linear soft tissue, the improved longitudinal tissue expander comprising:
   a) an inflatable expansion member, said expansion member further comprising an elastomeric expandable container having an upper and lower exterior surface, the interior of the container being in fluid communication with an external fluid reservoir by connecting means;
   b) a base affixed to said lower exterior surface of said expandable container; and
   c) a retaining disk affixed to the upper exterior surface of said expandable container.

2. The longitudinal tissue expander of claim 1 wherein said retaining disk is a substantially planar sheet of reinforced biocompatible material.

3. The longitudinal tissue expander of claim 2 wherein the area of attachment of the retaining disk to the upper exterior surface of the expandable container does not exceed ten percent of the total area of the upper exterior surface of the expandable container.

4. The longitudinal tissue expander of claim 2 wherein said reinforced biocompatible material is polyethalene-terephthalate fiber reinforced silicone.

* * * * *